(12) United States Patent
State et al.

(10) Patent No.: US 11,708,128 B2
(45) Date of Patent: Jul. 25, 2023

(54) SYSTEMS AND METHODS FOR EVALUATING AND REDUCING NEGATIVE DYSPHOTOPSIA

(71) Applicant: AMO Groningen B.V., Groningen (NL)

(72) Inventors: Mihai State, Groningen (NL); Robert Rosen, Groningen (NL); Sieger Meijer, Groningen (NL); Aixa Alarcon Heredia, Groningen (NL); Carmen Canovas Vidal, Groningen (NL)

(73) Assignee: AMO Groningen B.V., Groningen (NL)

( * ) Notice: Subject to any disclaimer, the term of this patent is extended or adjusted under 35 U.S.C. 154(b) by 57 days.

(21) Appl. No.: 17/057,634

(22) PCT Filed: Nov. 29, 2019

(86) PCT No.: PCT/EP2019/083179
§ 371 (c)(1),
(2) Date: Nov. 20, 2020

(87) PCT Pub. No.: WO2020/109602
PCT Pub. Date: Jun. 4, 2020

(65) Prior Publication Data
US 2021/0279939 A1      Sep. 9, 2021

Related U.S. Application Data

(60) Provisional application No. 62/773,983, filed on Nov. 30, 2018.

(51) Int. Cl.
*G06T 15/06* (2011.01)
*G06T 17/00* (2006.01)
(Continued)

(52) U.S. Cl.
CPC .............. *B62M 11/06* (2013.01); *A61F 2/164* (2015.04); *A61F 2/1645* (2015.04); *G02C 7/049* (2013.01);
(Continued)

(58) Field of Classification Search
CPC .......... B62M 11/06; B62M 1/36; A61F 2/164; A61F 2/1645; A61F 2/16;
(Continued)

(56) References Cited

U.S. PATENT DOCUMENTS

2005/0041203 A1     2/2005  Lindacher et al.
2006/0241751 A1 *  10/2006  Marmo ................. A61F 2/1453
                                                         623/5.11
(Continued)

FOREIGN PATENT DOCUMENTS

WO          2010100523 A1      9/2010

OTHER PUBLICATIONS

Curcio C, C., et al., "Human Photoreceptor Topography," The Journal of Comparative Neurology, 1990, vol. 292, pp. 497-523.
(Continued)

*Primary Examiner* — Siamak Harandi
(74) *Attorney, Agent, or Firm* — Johnson & Johnson Surgical Vision, Inc.

(57) ABSTRACT

Systems and methods for evaluating ND are described herein. An example method can include constructing a non-sequential (NSC) ray-tracing model of an eye with an ophthalmic lens, and modelling a light source and a detector. The detector can be configured to mimic a retina of the eye. The method can also include computing irradiance data using the light source, the NSC ray-tracing model, and the detector. Irradiance data can be computed for each of a plurality of pupil sizes. The method can further include evaluating ND by analyzing the respective irradiance data
(Continued)

for each of the pupil sizes. Also described herein are methods for designing an ophthalmic lens edge that reduces the incidence of ND for a given ophthalmic lens by adjusting the edge thickness and/or the scatter.

23 Claims, 10 Drawing Sheets (51) Int. Cl.
  *B62M 11/06* (2006.01)
  *A61F 2/16* (2006.01)
  *G02C 7/04* (2006.01)
  *G06T 7/00* (2017.01)
  *B62M 1/36* (2013.01)
(52) U.S. Cl.
  CPC ............ *G06T 7/0012* (2013.01); *G06T 15/06* (2013.01); *G06T 17/00* (2013.01); *B62M 1/36* (2013.01); *G06T 2207/30041* (2013.01); *G06T 2210/41* (2013.01); *G06T 2215/16* (2013.01)
(58) Field of Classification Search
  CPC ... A61F 2240/002; G02C 7/049; G02C 7/028; G06T 7/0012; G06T 15/06; G06T 17/00; G06T 2207/30041; G06T 2210/41; G06T 2215/16; G16H 50/50
  See application file for complete search history.

(56) References Cited

U.S. PATENT DOCUMENTS

2008/0269885 A1  10/2008  Simpson et al.
2008/0269886 A1* 10/2008  Simpson ............... A61F 2/1654
                                           623/6.31
2008/0269890 A1  10/2008  Simpson et al.

OTHER PUBLICATIONS

Curcio C.A., et al., "Topography of Ganglion Cells in Human Retina," The Journal of Comparative Neurology, 1990, vol. 300, pp. 5-25.
Holladay J.T., et al., "Negative Dysphotopsia: The Enigmatic Penumbra," Journal Cataract and Refractive Surgery, Jan. 2012, vol. 38 (7), pp. 1251-1265.
Hong X., et al, "Ray-Tracing Optical Modeling of Negative Dysphotopsia," Journal of Biomedical Optics, Dec. 2011, vol. 16(12), pp. 125001.
International Search Report and written opinion for Application No. PCT/EP2019/078555, dated Mar. 30, 2020, 12 pages.
International Search Report and Written Opinion for Application No. PCT/EP2019/083179, dated Feb. 6, 2020, 14 pages.
Spector R.H., "Chapter 116 Visual Fields Figure 116.1" Clinical Methods: The History, Physical, and Laboratory Examinations, 3rd Edition Walker HK, Hall WD, Hurst JW 1990, Retrieved from the Internet: (https://www.ncbi.nlm.nih.gov/books/NBK220/), 8 Pages.

* cited by examiner

SYSTEMS AND METHODS FOR EVALUATING AND REDUCING NEGATIVE DYSPHOTOPSIA

CROSS REFERENCE TO RELATED APPLICATIONS

This application is a U.S. national stage of and claims the benefit under 35 U.S.C. § 371 of International Patent Application No. PCT/EP2019/083179, filed Nov. 29, 2019, which claims priority to, and the benefit of, under 35 U.S.C. § 119(e) of U.S. Provisional Appl. No. 62/773,983, filed Nov. 30, 2018, all of which are incorporated by reference herein in their entirety.

BACKGROUND

Negative dysphotopsia (ND) is characterized by subjective reports and complaints from patients having an intraocular lens (IOL) implanted, where the complaints describe the presence of a dark shadow in the far periphery. A number of patient factors, including small photopic pupil, high angle kappa and hyperopia, have been identified as increasing the risk of ND. The presence of ND is likely caused by absence of light in the retinal interval between light passing through and refracted by the IOL (e.g., at lower angles of incidence) and rays missing the IOL (e.g., at higher angles of incidence). While the light passing the IOL at the lower angles of incidence is refracted, changing its direction to a lower angle, the light at the higher angles miss the IOL and continue straight without deviation, thereby creating an angular interval on the retina that is not illuminated. The problem is partially alleviated at larger pupil sizes, since optical errors create larger deviations of rays at the pupil edge which partially hits the obscured part of the peripheral retina. On the other hand, for smaller pupils the pinhole effect exacerbates the ND effect. For the natural crystalline lens, ND is not a problem, since no light will miss the lens as it is larger and closer to the pupil.

SUMMARY

An example computer-implemented method for evaluating negative dysphotopsia (ND) is described herein. The method can include constructing a non-sequential (NSC) ray-tracing model of an eye with an ophthalmic lens, and modelling a light source and a detector, where the detector is configured to mimic a retina of the eye. The method can also include for each of a plurality of pupil sizes, computing irradiance data using the light source, the NSC ray-tracing model, and the detector. The method can further include evaluating ND by analyzing the respective irradiance data for each of the pupil sizes.

In some implementations, the step of analyzing the respective irradiance data for each of the pupil sizes can include determining a retinal illumination gap between light refracted by the ophthalmic lens and light refracted only by a cornea of the eye.

Alternatively or additionally, the respective irradiance data in the temporal visual field can be analyzed.

Alternatively or additionally, the irradiance data can be at least one of an irradiance map or a cross-sectional irradiance profile. For example, in some implementations, the irradiance data can be a cross-sectional irradiance profile, and the method can further include deriving at least one of ND angular location, ND angular width, local contrast, or local area of reciprocal irradiance using the cross-sectional irradiance profile.

Alternatively or additionally, the method can further include constructing a sequential ray-tracing model of the eye using biometrical patient data.

Alternatively or additionally, the ophthalmic lens can be modeled as a three-dimensional (3D) object. Optionally, the method can include generating a 3D model of the ophthalmic lens. Optionally, the method can include adjusting the position or orientation of the 3D object within the eye.

Alternatively or additionally, the light source can be a wide angle high divergence light source.

Alternatively or additionally, the detector can be a spherical or aspherical detector. Optionally, in some implementations, the detector can be defined by an aspheric equation or a toric aspheric equation.

Alternatively or additionally, the method can optionally further include constructing a respective NSC ray-tracing model of the eye with each of a plurality of ophthalmic lenses, where each of the ophthalmic lenses is configured for a different degree of edge scattering, and for each of the pupil sizes, computing irradiance data using the light source, the respective NSC ray-tracing models, and the detector. The method can optionally further include selecting an ophthalmic lens design that reduces ND from the plurality of ophthalmic lenses.

Alternatively or additionally, the method can optionally further include constructing a respective NSC ray-tracing model of the eye with each of a plurality of ophthalmic lenses, where each of the ophthalmic lenses has a different edge thickness, and for each of the pupil sizes, computing irradiance data using the light source, the respective NSC ray-tracing models, and the detector. The method can optionally further include selecting an ophthalmic lens design that reduces ND from the plurality of ophthalmic lenses.

Alternatively or additionally, the ophthalmic lens can be an intraocular lens (IOL).

Another example computer-implemented method for reducing the detectability of negative dysphotopsia (ND) is described herein. The method can include constructing a respective NSC ray-tracing model of the eye with an ophthalmic lens for each of a plurality of different ophthalmic lens edge designs, and modelling a light source and a detector, where the detector is configured to mimic a retina of the eye. The method can also include, for each of a plurality of pupil sizes, computing irradiance data using the light source, the respective NSC ray-tracing models, and the detector, evaluating ND by analyzing the respective irradiance data for each of the pupil sizes, and selecting one of the different ophthalmic lens edge designs to reduce ND.

Alternatively or additionally, the one of the different ophthalmic lens edge designs can reduce a retinal illumination gap between light refracted by the ophthalmic lens and light refracted only by a cornea of the eye. In some implementations, the one of the different ophthalmic lens edge designs can minimize the retinal illumination gap between light refracted by the ophthalmic lens and light refracted only by a cornea of the eye.

Alternatively or additionally, the method can further include optimizing the ophthalmic lens edge design for a given optics diameter and/or for a given ophthalmic lens material.

Alternatively or additionally, the different ophthalmic lens edge designs can be different Lambertian scattering coefficients.

Alternatively or additionally, the different ophthalmic lens edge designs can be different edge thicknesses.

An example method for manufacturing an ophthalmic lens is also described herein.

An example method for creating a physical eye model including an ophthalmic lens is also described herein.

An example method for indirectly quantifying edge frosting effect of an ophthalmic lens is also described herein. The method can include obtaining measurements using an off-axis modulation transfer function (MTF) bench, the physical eye model as describe herein, and an electronic light sensor. The method can further include quantifying edge frosting effect of the ophthalmic lens by inputting the measurements into a non-sequential (NSC) ray-tracing model of an eye with an ophthalmic lens.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations are described for intraocular lenses, it will become evident to those skilled in the art that the implementations are not limited thereto, but are applicable for other ophthalmic lenses.

As used herein, the terms "light" or "visible light" mean electromagnetic radiation within the visible waveband, for example, electromagnetic radiation with a wavelength in a vacuum that is between 390 nanometers and 780 nanometers. As used herein, the term "optical power" of a lens or optic means the ability of the lens or optic to converge or diverge light to provide a focus (real or virtual) when disposed within a media having a refractive index of 1.336 (generally considered to be the refractive index of the aqueous and vitreous humors of the human eye), and is specified in reciprocal meters or Diopters (D). See ISO 11979-2. As used herein the terms "focus" or "focal length" of a lens or optic is the reciprocal of the optical power. As used herein the term "power" of a lens or optic means optical power. Except where noted otherwise, optical power (either absolute or add power) of an intraocular lens or associated optic is from a reference plane associated with the lens or optic (e.g., a principal plane of an optic).

As used herein, the term "near vision" means vision produced by an eye that allows a subject to focus on objects that are at a distance of 40 cm or closer to a subject, typically within a range of 25 cm to 33 cm from the subject, which corresponds to a distance at which a subject would generally place printed material for the purpose of reading. As used herein, the term "intermediate vision" means vision produced by an eye that allows a subject to focus on objects that are located between 40 cm and 2 meters from the subject. As used herein, the term "distant vision" means vision produced by an eye that allows a subject to focus on objects that are at a distance that is greater than 2 meters, typically at a distance of about 5 meters from the subject, or at a distance of about 6 meters from the subject, or greater.

Figure 1A:
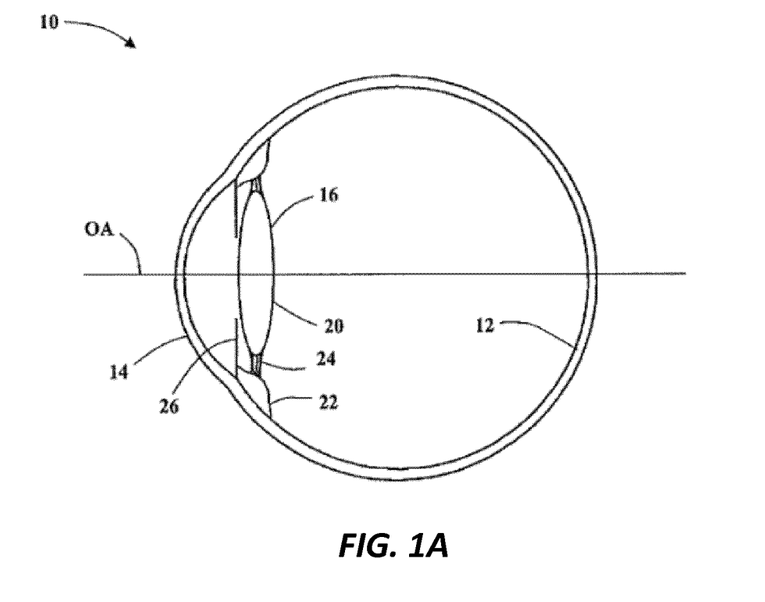
FIG. 1A illustrates a side view of an eye containing a natural crystalline lens.

Referring now to FIG. 1A, a cross-sectional view of a phakic eye containing the natural crystalline lens is shown in which an eye 10 includes a retina 12 that receives light in the form of an image produced when light from an object is focused by the combination of the optical powers of a cornea 14 and a natural crystalline lens 16. The cornea 14 and lens 16 are generally disposed about an optical axis (OA). As a general convention, an anterior side is considered to be a side closer to the cornea 14, while a posterior side is considered to be a side closer to the retina 12.

The natural lens 16 is enclosed within a capsular bag 20, which is a thin membrane attached to a ciliary muscle 22 via zonules 24. An iris 26, disposed between the cornea 14 and the natural lens 16, provides a variable pupil that dilates under lower lighting conditions (mesopic or scotopic vision) and constricts under brighter lighting conditions (photopic vision). The ciliary muscle 22, via the zonules 24, controls the shape and position of the natural lens 16, allowing the eye 10 to focus on both distant and near objects. It is generally understood that distant vision is provided when the ciliary muscle 22 is relaxed, wherein the zonules 24 pull the natural lens 16 so that the capsular bag 20 and lens 16 are generally flatter and provide a longer focal length (lower optical power). It is generally understood that near vision is provided when the ciliary muscle contracts, thereby relaxing the zonules 24 and allowing the capsular bag 20 and lens 16 to return to a more rounded state that produces a shorter focal length (higher optical power).

Figure 1B:
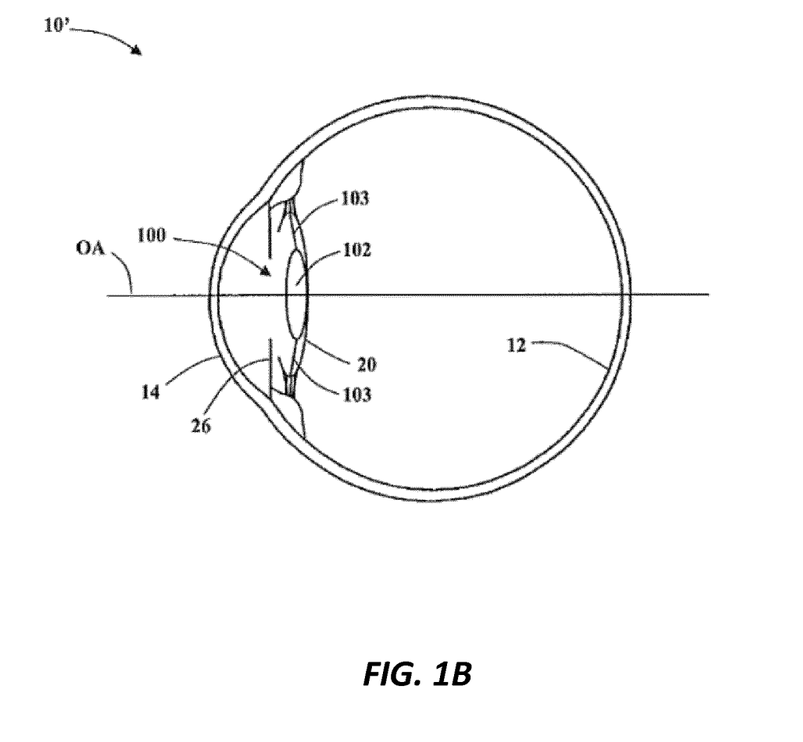
FIG. 1B illustrates a side view of the eye shown in FIG. 1A with an IOL.

Referring now to FIG. 1B, a cross-sectional view of a pseudophakic eye is shown in which the natural crystalline lens 16 has been replaced by an intraocular lens 100 according to an implementation described herein. The intraocular lens 100 can include an optic 102 and haptics 103, the haptics 103 being configured to at least generally center the optic 102 within the capsular bag 20, provide transfer of ocular forces to the optic 102, and the like. Numerous configurations of haptics 103 relative to optic 102 are well known within the art, and the optics edge designs described herein can generally include any of these haptic configurations. Moreover, this disclosure contemplates that the methods described herein can be used to evaluate any IOL independently of the haptics configuration and/or optics design.

Figure 2:
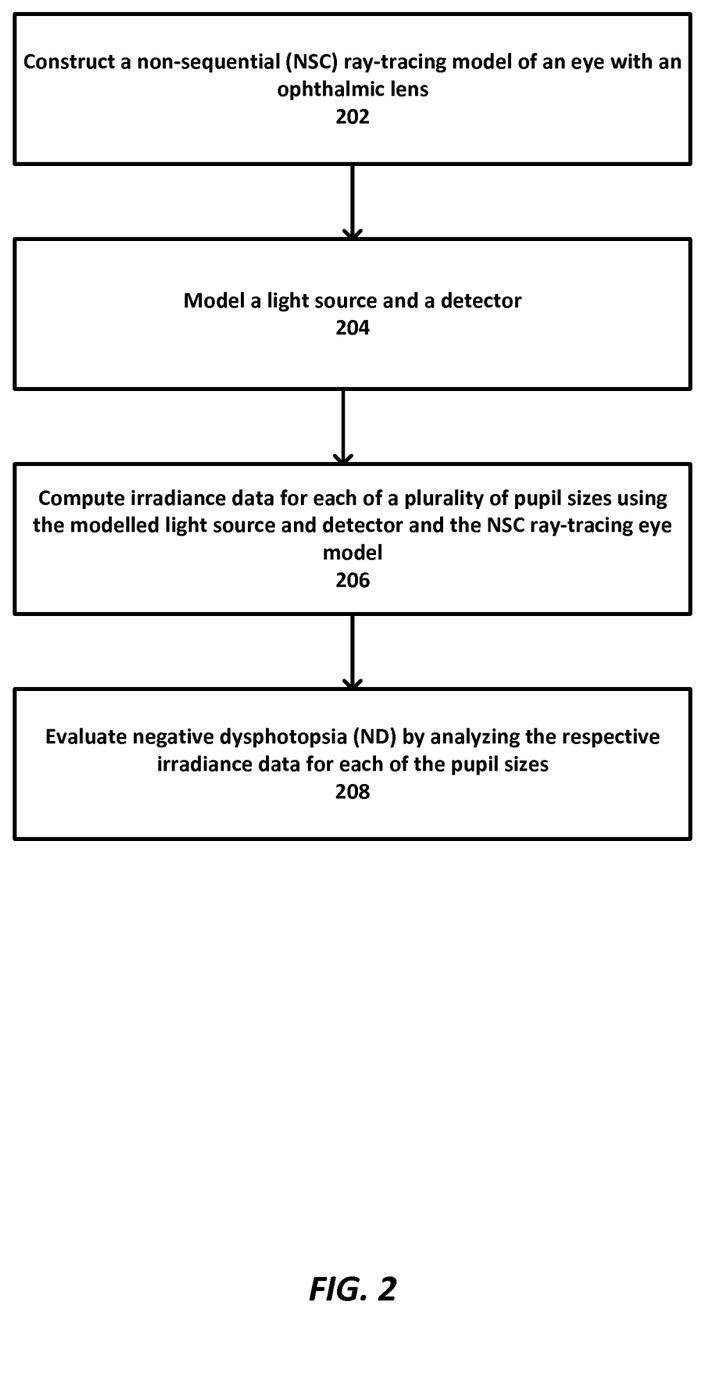
FIG. 2 is a flow chart illustrating example operations for evaluating negative dysphotopsia according to an implementation described herein.
Figure 3:
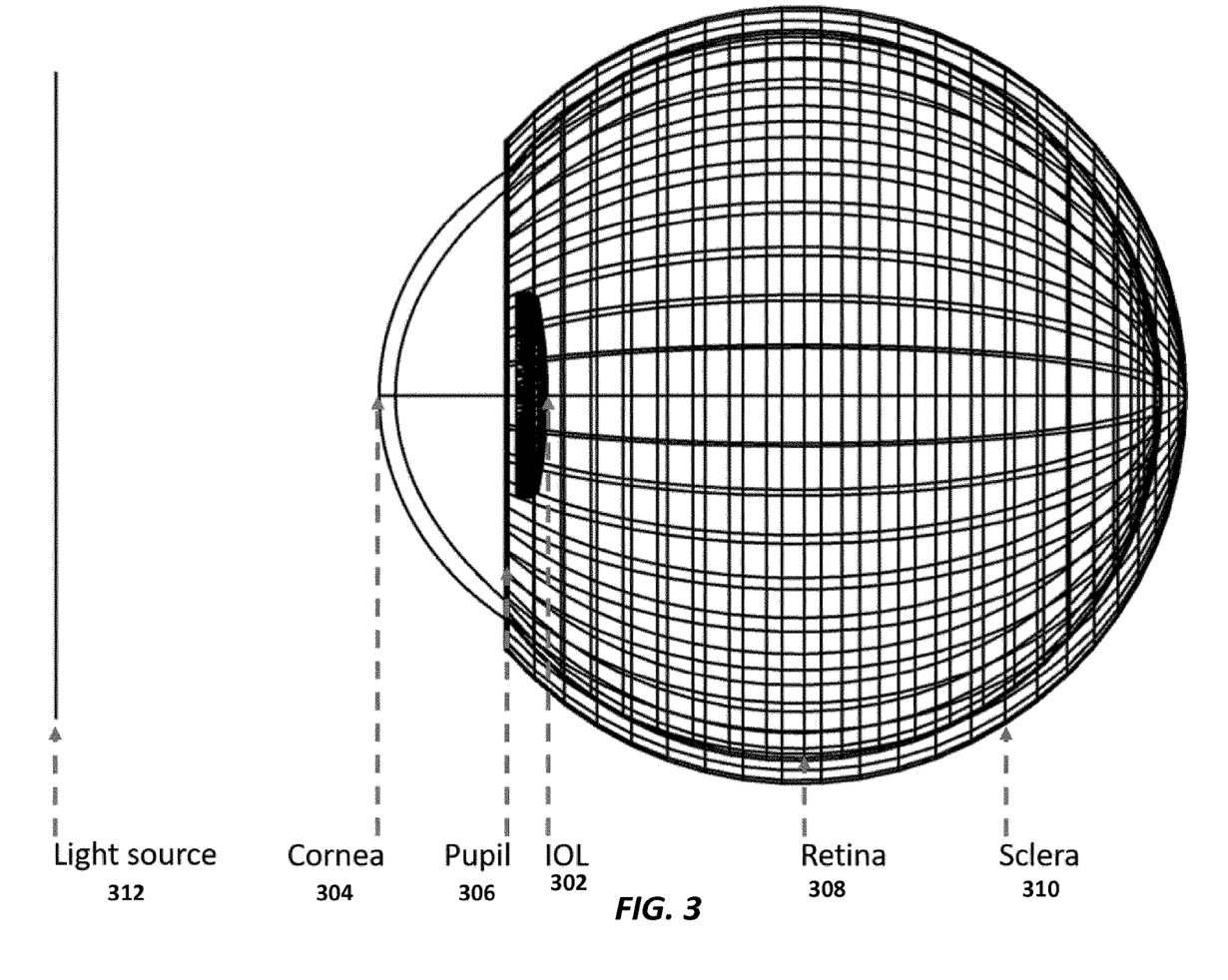
FIG. 3 is a schematic depiction of a non-sequential ray-tracing eye model of an eye with an ophthalmic lens according to an implementation described herein.

Referring now to FIG. 2, example operations for evaluating ND are described. The operations can be used to evaluate ND in clinically resembling conditions. This disclosure contemplates that the operations can be performed by a computing device (e.g., computing device 900 as described with respect to FIG. 9). Additionally, this disclosure contemplates that the operations can be performed with optical design software running on a computing device. OPTICSTUDIO from Zemax, LLC of Kirkland, Wash. and OSLO from Lambda Research Corporation of Littleton, Mass. are examples of optical design software. At step 202, a non-sequential (NSC) ray-tracing model of an eye with an ophthalmic lens can be constructed. In an NSC ray-tracing model, the objects (e.g., ophthalmic lens, pupil of the eye, etc.) that rays hit are determined by the physical positions of the objects, characteristics of the objects, and/or directions of the rays. A ray may hit some objects, even multiple times, while missing other objects. This is in contrast to sequential ray tracing, where every ray passes through the same objects and in the same order. Sequential and non-sequential ray-tracing are known in the art and are therefore not described in further detail herein. The ophthalmic lens can optionally be an intraocular lens. Although an intraocular lens is used in the examples below, it should be understood that the methods described herein are applicable to other ophthalmic lenses. The ophthalmic lens can be modeled as a three-dimensional (3D) object. For example, a 3D model of the ophthalmic lens can be generated as a 3D computer aided design (CAD) object. Optionally, the position or orientation of the 3D object within the eye model can be adjusted. An example NSC ray-tracing model of the eye with an intraocular lens 302 (e.g., an ophthalmic lens) is shown in FIG. 3. The NSC ray-tracing model of FIG. 3 includes the cornea 304, pupil 306, retina 308, and sclera 310.

Optionally, in some implementations, a sequential ray-tracing model of the eye can be constructed with and validated against individualized biometrical patient data. Such individualized biometrical data can include, but is not limited to, pupil size, anterior chamber depth, distance iris—IOL, axial length, anterior corneal topography, IOL tilt and decentration, and post-operative refractive errors. One example sequential ray-tracing eye model is the Liou-Brennan human eye model. The Liou-Brennan human eye model is only provided as an example, and it should be understood that other sequential eye models such as the TECNIS Chromatic Eye model from JOHNSON & JOHNSON of New Brunswick, N.J. can be used. Then, using the same biometry, the NSC ray-tracing model of the eye with an ophthalmic lens can be constructed (e.g., step 202).

At step 204, a light source and a detector can be modelled. The light source 312 can be a wide angle high divergence mono or polychromatic light source. The light source 312 is shown in the NSC ray-tracing model of FIG. 3. This disclosure contemplates that the modelled light source can be another type of light source including, but not limited to a collimated light source positioned at certain eccentricity. The light source 312 can illuminate the detector. Additionally, the detector can be a spherical or aspherical detector (discretized in Cartesian or polar coordinates). For example, the detector can mimic the retinal shape by means of an aspheric equation or a toric aspheric equation. The angular extent of the detector can optionally match the peripheral location of ora serrata or the quadrantic visual field limits, and the pixel size of the detector can optionally be smaller than the peripheral sampling of the photoreceptors. C. A. Curcio et al., THE JOURNAL OF COMPARATIVE NEUROLOGY 292:497-523 (1990); C. A. Curcio et al., THE JOURNAL OF COMPARATIVE NEUROLOGY 300:5-25 (1990). In some implementations, the detector can optionally have greater than 90 degrees maximum extent with less than 2.5 degrees pixel size in both azimuthal and radial directions. Additionally, the detector can optionally account for retinal asymmetries between different meridians such as the vertical and the horizontal meridians (e.g., by defining the detector using a toric aspheric equation). This disclosure contemplates that the modelled detector can have characteristics other than those above, which are only provided only as examples.

Figure 4:
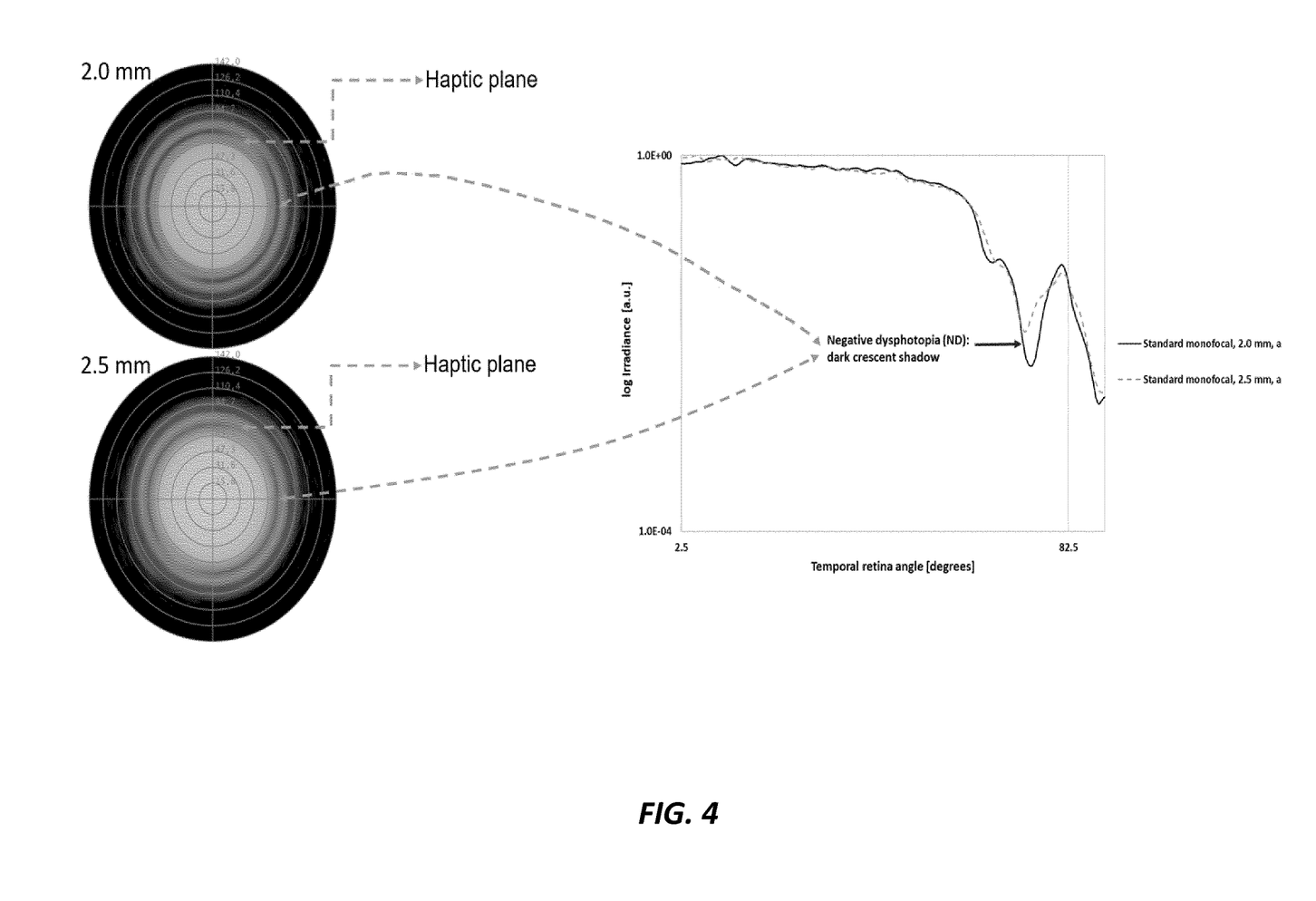
FIG. 4 illustrates the results of computing irradiance data (retinal irradiance maps and cross-sectional irradiance profiles) according to an implementation described herein.

At step 206, irradiance data can be computed. In other words, irradiance data can be simulated using the modelled light source and detector, as well as the NSC ray-tracing model (e.g., as shown by FIG. 3). Irradiance data can be computed for each of a plurality of pupil sizes (e.g., for different pupil sizes). Irradiance data can include, but is not limited to, an irradiance map and/or a cross-sectional irradiance profile. FIG. 4 illustrates example retinal irradiance maps and cross-sectional irradiance profiles computed as described above. This disclosure contemplates that the cross-sectional irradiance profile can be used for deriving quantitative information (also referred to herein as "figures of merit") including, but not limited to, ND angular location, ND angular width, local contrast, and local area of the reciprocal irradiance.

At step 208, ND can be evaluated by analyzing the irradiance data. In some implementations, this can include analyzing the figures of merit described above, e.g., the quantitative information derived from a cross-sectional irradiance profile. In other implementations, this can include determining a retinal illumination gap between light refracted by the ophthalmic lens and light refracted only by a cornea of the eye. The analysis can be performed on the respective irradiance data for each of the pupil sizes. Due to the pinhole effect, smaller pupils are associated with a higher incidence of ND complaints. For example, when using a standard monofocal IOL, FIG. 4 demonstrates that the NSC eye-model retains its clinical relevance in terms of angular location of ND (e.g., approximately 75 degrees) and ND dependency with pupil size (e.g., optical errors determine larger ray deviations filling the retinal illumination gap).

The irradiance data computations described above are conducted using a rotationally symmetric eye model (e.g., the NSC ray-tracing model shown in FIG. 3). Such a model neglects the visual field limiting impact of surrounding bone structures (e.g., supraorbital margin, nasal and zygomatic bones) of the subject such as a human being. In other words, irradiance data is obtained for all of the temporal, nasal, inferior, and superior visual fields. In practical applications, the monocular visual field limits for a human being are about: 90° temporal, 60° nasal, 70° inferior, and 50° superior. Millodot, M., *Dictionary of Optometry and Visual Science*, Oxford: Butterworth-Heinemann, $4^{th}$ ed., 1997. These visual field limits explain why ND is typically reported in the temporal visual field. The temporal visual field is the only quadrant having an extent larger than the angular location of ND (e.g., about 75 degrees). Thus, in some implementations, the irradiance data in the temporal visual field can be analyzed. In other words, the irradiance data in one or more of the nasal, inferior, and superior visual fields can be ignored if surrounding bone structures limit the extent in these quadrants such that ND may not be detected by the subject in these quadrants.

Figure 5:
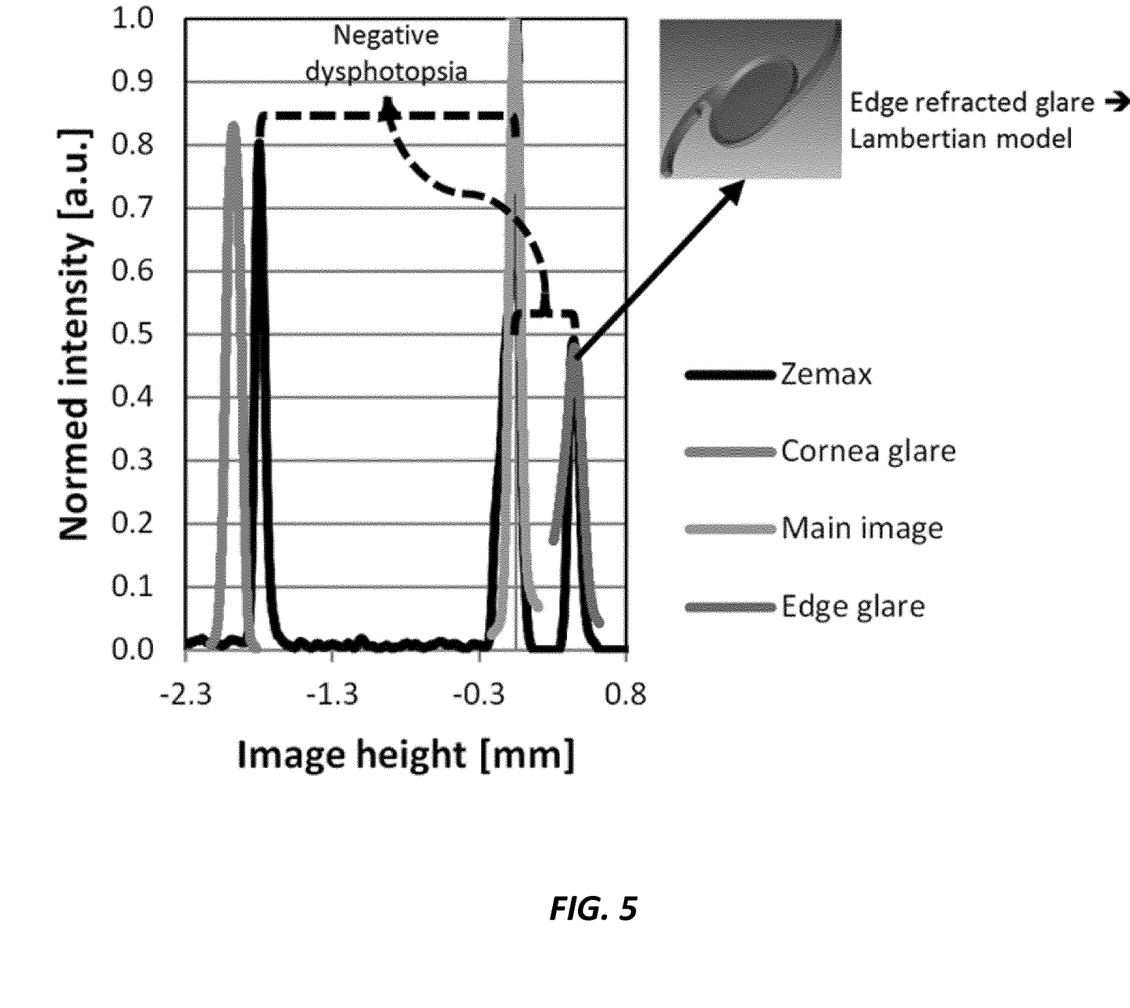
FIG. 5 illustrates the results of edge scattering modelling according to an implementation described herein.

For the purpose of reducing positive dysphotopsia (PD), which is subjectively perceived spurious bright images in scotopic conditions, caused by IOL edge-reflected light, the edges of IOLs can be roughened to various extents during manufacturing, which promotes light scattering. Roughening depends on the manufacturer and fabrication method. To account for the IOL edge glare relative intensity, the edge frosting effect can be retro-fitted by a Lambertian scattering surface to measurements performed by means of an off-axis modulation transfer function (MTF) bench, a physical wide angle eye model fitted with an IOL (e.g., the physical eye model shown in FIG. 10), and a charge-coupled device (CCD) camera. FIG. 5 illustrates edge scattering modelling results where the Lambertian scattering coefficient (a) is retro-fitted to measurements.

Figure 6:
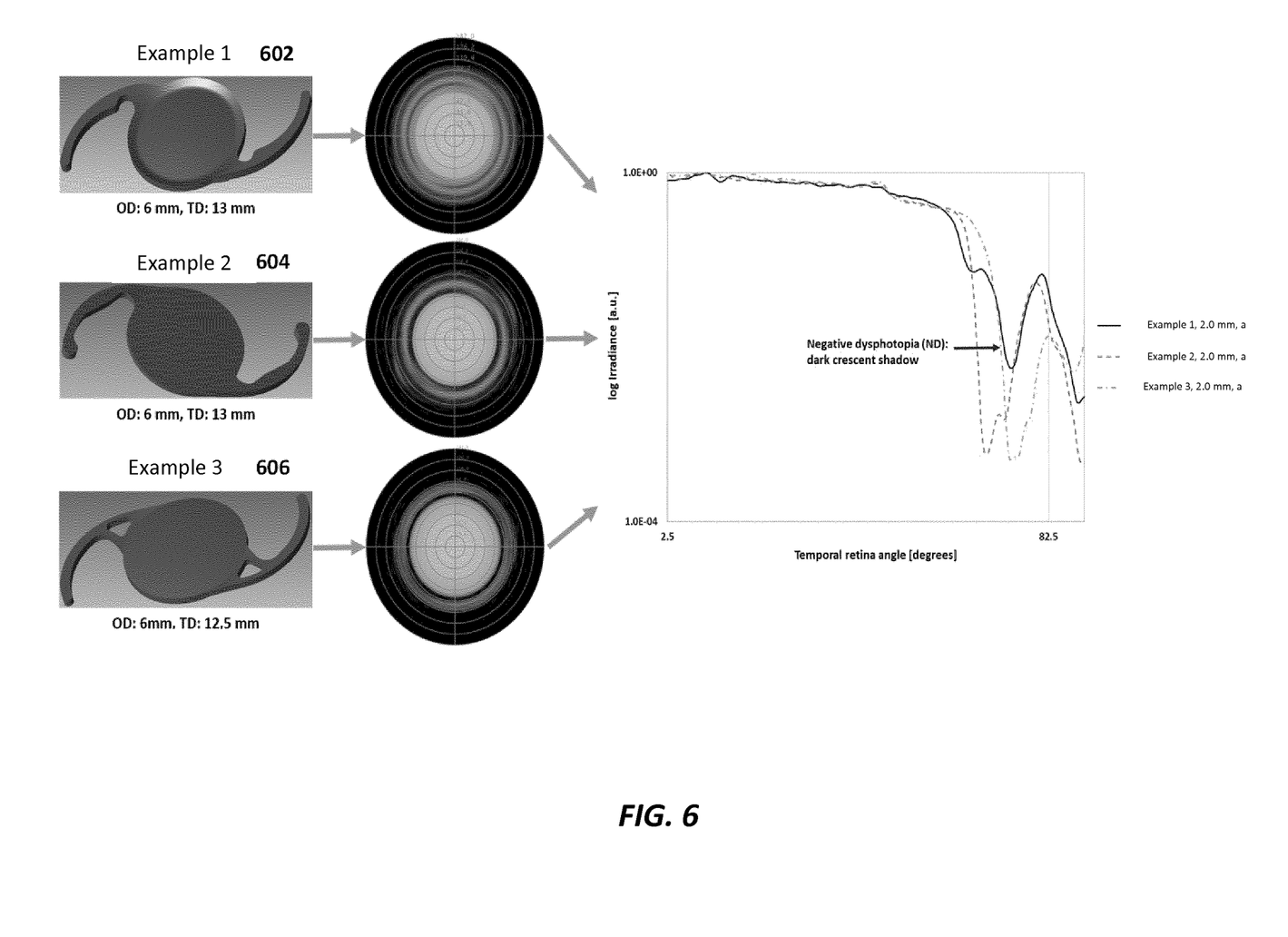
FIG. 6 illustrates the negative dysphotopsia profiles of various IOL designs.

Referring now to FIG. 6, ND profiles of various IOL mechanical platform designs are described. Across manufacturers, while the optic edge designs differ (e.g., surface roughness, thickness, IOL material refractive index, etc.), existing IOL mechanical platforms tend to be characterized by relatively similar geometries, for example, optic diameter of about 6 mm, total diameter between about 12.5-13.0 mm, and haptic loop designs. In FIG. 6, the ND profiles for three commercially available example IOL platforms are shown. The commercially available platforms are labeled standard monofocal, "Example 1" 602, "Example 2" 604, and "Example 3" 606. These IOL platforms are modelled with Lambertian edge scattering, 2 mm entrance pupil, optic body diameter (OD), and total diameter (TD). FIG. 6 shows that in identical biometrical conditions, these similar IOL mechanical platforms designs with different edge designs are characterized by similar ND profiles. In FIG. 6, all of the simulations used the same Lambertian edge scattering coefficient (a).

Optionally, the methods described herein can be used to evaluate a plurality of ophthalmic lens designs, where each design is configured with a different degree of edge scattering. Using the results of such evaluation, an ophthalmic lens design that reduces ND can be selected. For example, a respective NSC ray-tracing model of the eye with each of a plurality of ophthalmic lenses, where each of the ophthalmic lenses is configured for a different degree of edge scattering, can be constructed. Thereafter, irradiance data can be computed as described herein and using each of the respective NSC ray-tracing models. This data can be analyzed to evaluate ND, and an ophthalmic lens design that reduces ND can be selected. This disclosure contemplates that ophthalmic lenses having the selected design can then be manufactured.

Optionally, the methods described herein can be used to evaluate a plurality of ophthalmic lens designs, where each design has a different edge thickness. Using the results of such evaluation, an ophthalmic lens design that reduces ND can be selected. For example, a respective NSC ray-tracing model of the eye with each of a plurality of ophthalmic lenses, where each of the ophthalmic lenses has a different edge thickness, can be constructed. Thereafter, irradiance data can be computed as described herein and using each of the respective NSC ray-tracing models. This data can be analyzed to evaluate ND, and an ophthalmic lens design that reduces ND can be selected. This disclosure contemplates that ophthalmic lenses having the selected design can then be manufactured.

In some implementations, the ophthalmic edge design can optionally be optimized for a given optics diameter. For example, as described herein, an objective of the evaluation is to reduce, and in some implementations, minimize the retinal illumination gap between light refracted by the ophthalmic lens and light refracted only by the cornea of the eye. Thus, for a given optics diameter, based on the angular location of ND and the irradiance drop associated with ND, the degree of edge scattering and/or the edge thickness can be increased to minimize the retinal illumination gap. Similarly, the ophthalmic edge design can optionally be optimized for a given ophthalmic lens material. In this case, for a given refractive index, based on the angular location of ND and the irradiance drop associated with ND, the degree of edge scattering and/or the edge thickness can be increased to minimize the retinal illumination gap. This disclosure contemplates that ophthalmic lenses having the optimal design can then be manufactured.

Figure 7:
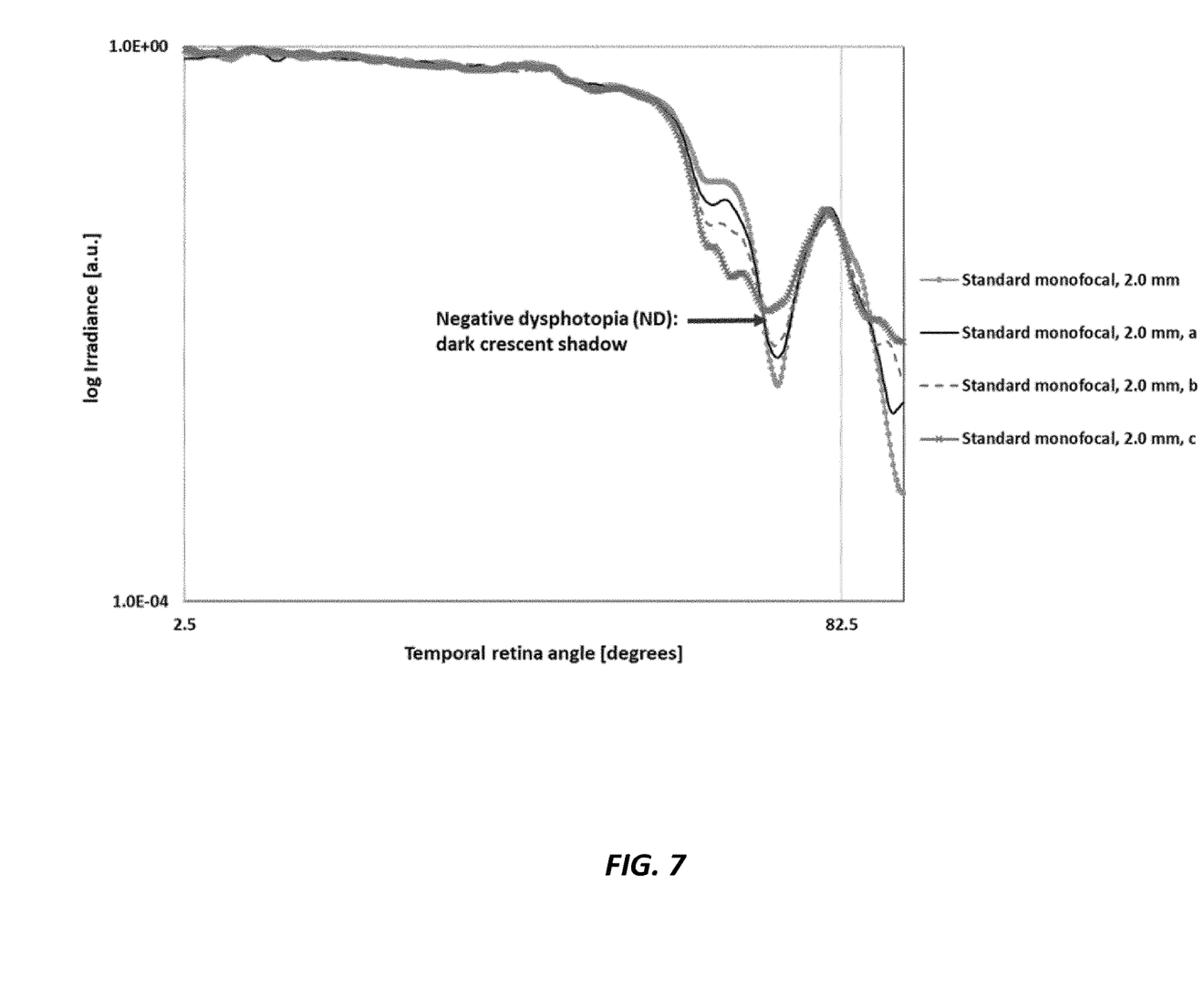
FIG. 7 illustrates simulated irradiance retinal profiles for a standard monofocal IOL without edge scattering (e.g., with a smooth surface) and with various degrees of edge scattering.

The methods described herein can be used to design an ophthalmic lens edge, where the edge design is defined by the Lambertian scattering coefficient. Using the methods described herein, an ophthalmic lens edge scatter that reduces ND can be selected for a given IOL platform. For example, the ophthalmic lens edge scatter can be adjusted to reduce the retinal illumination gap between light refracted by the ophthalmic lens and light refracted only by a cornea of the eye. An ophthalmic lens edge design (e.g., the Lambertian scattering coefficient) that reduces, and in some implementations minimizes, the retinal illumination gap can be selected. For example, in FIG. 7, the simulated irradiance retinal profiles include those for a standard monofocal IOL without edge scattering and a standard monofocal IOL with various edge scattering coefficients (e.g., the Lambertian scattering coefficient (a) in FIG. 5, 2×Lambertian scattering coefficient (a)=Lambertian scattering coefficient (b), and 3×Lambertian scattering coefficient (a)=Lambertian scattering coefficient (c)). It should be understood that the values of the Lambertian scattering coefficient used for the simulations in FIG. 7 are provided only as examples and that other values can be used. Part of the edge scattered light is filling the retinal illumination gap. From a contrast threshold ND detection mechanism point of view, by reducing the local irradiance contrast it is possible to lower the likelihood of the subject complaining about ND. This disclosure contemplates that the edge of an IOL can be roughened by lathing/milling parameters, which include but are not limited to tool radius, feed rate, tool RPM, etc., and/or any other suitable fabrication process such as photo-lithography, printing, molding, embossing, spin coating, dry etching etc.

Figure 8:
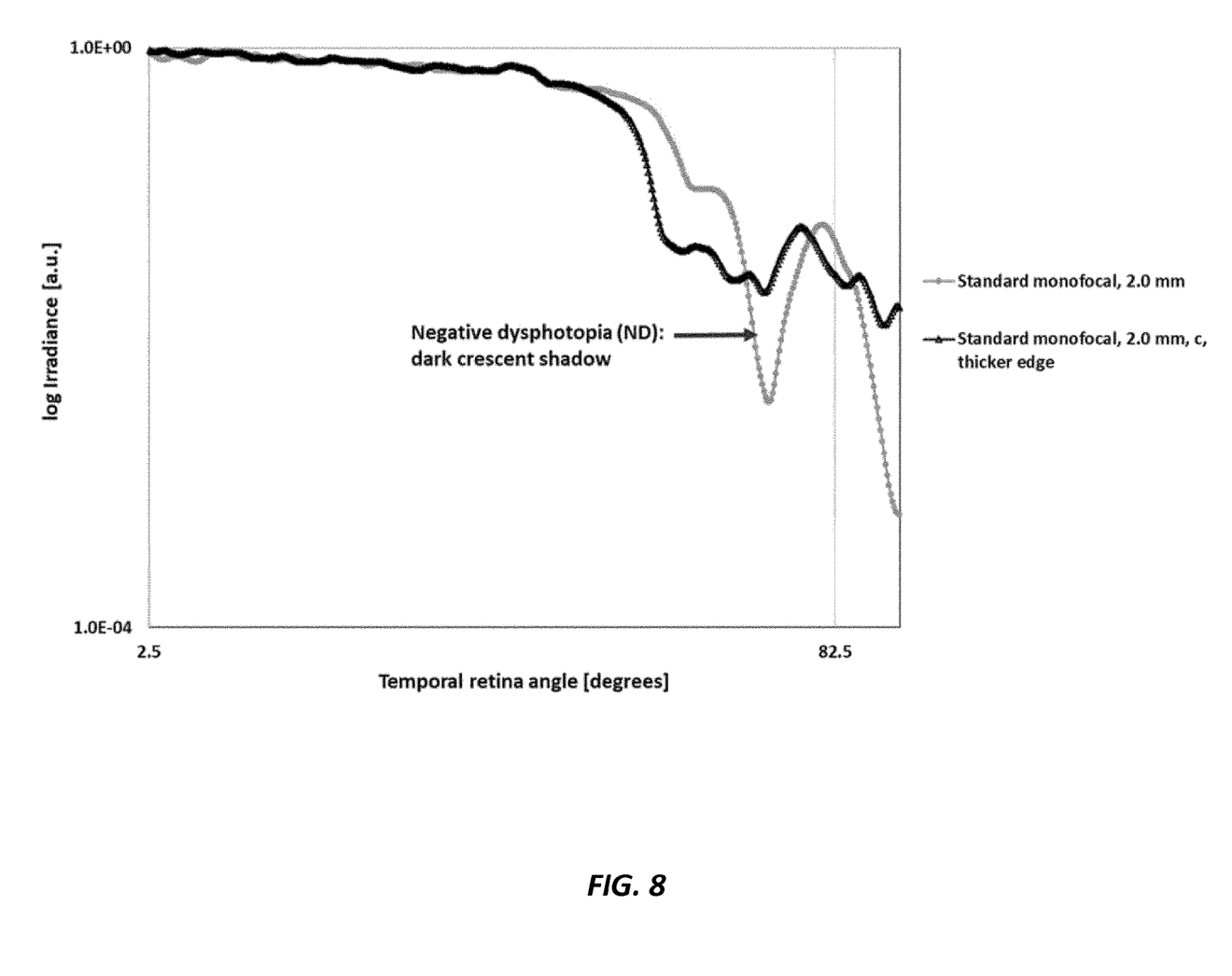
FIG. 8 illustrates simulated irradiance retinal profiles for a standard monofocal IOL with various edge thicknesses.

Alternatively or additionally, the methods described herein can be used to design an ophthalmic lens edge, where the edge design is defined by the thickness. Using the methods described herein, an ophthalmic lens edge thickness that reduces ND can be selected for a given IOL platform. For example, the ophthalmic lens edge thickness can be adjusted to reduce the retinal illumination gap between light refracted by the ophthalmic lens and light refracted only by a cornea of the eye. An ophthalmic lens edge design (e.g., the edge thickness) that reduces, and in some implementations minimizes, the retinal illumination gap can be selected. For example, in FIG. 8, simulated irradiance retinal profiles for a standard monofocal IOL with various edge thicknesses are described. In addition to maximizing scattering with roughened edges, further alteration of the ND profile can be achieved by increasing the edge thickness of an IOL. FIG. 8 illustrates the effect of a 70% IOL edge thickness increase on the ND profile. In FIG. 8, the simulated irradiance retinal profile for a standard monofocal IOL (using the Lambertian scattering coefficient (a) in FIGS. 5 and 7) is compared with the simulated irradiance retinal profile for a standard monofocal IOL with 70% increased edge thickness (using the Lambertian scattering coefficient (c) in FIG. 7). It should be understood that the values of the Lambertian scattering coefficient and/or increased edge thickness used for the simulations in FIG. 8 are provided only as examples and that other values can be used.

It should be understood that the methods described herein for designing and manufacturing ophthalmic lens would require minimal manufacturing process adjustments and/or have a negligible impact on insertability and mechanical stability post-implantation.

Figure 9:
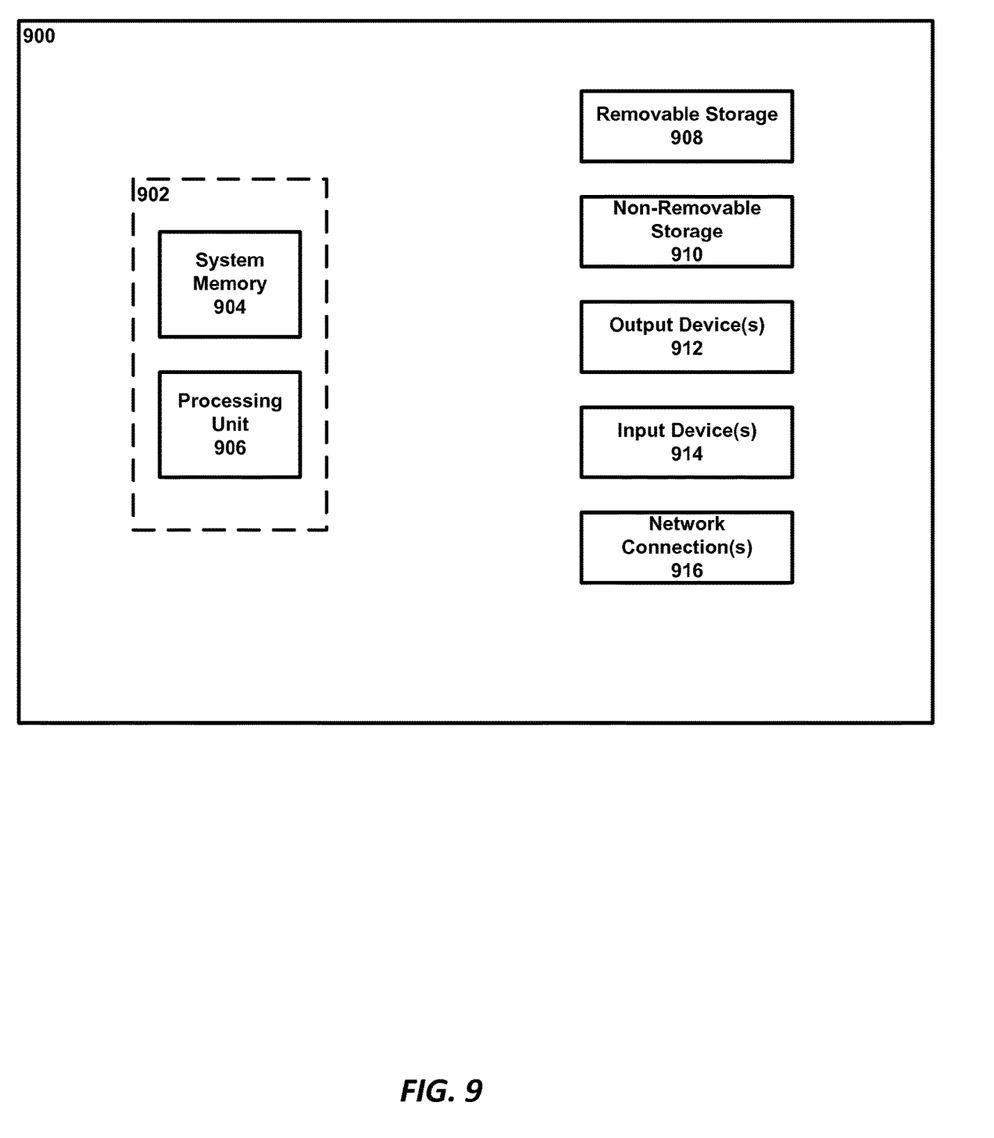
FIG. 9 is an example computing device.

It should be appreciated that the logical operations described herein with respect to the various figures may be implemented (1) as a sequence of computer implemented acts or program modules (i.e., software) running on a computing device (e.g., the computing device described in FIG. 9, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Referring to FIG. 9, an example computing device 900 upon which the methods described herein may be implemented is illustrated. It should be understood that the example computing device 900 is only one example of a suitable computing environment upon which the methods described herein may be implemented. Optionally, the computing device 900 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 900 typically includes at least one processing unit 906 and system memory 904. Depending on the exact configuration and type of computing device, system memory 904 may be volatile (such as random access memory (RAM)), non-volatile (such as read-only memory (ROM), flash memory, etc.), or some combination of the two. This most basic configuration is illustrated in FIG. 9 dashed line 902. The processing unit 906 may be a standard programmable processor that performs arithmetic and logic operations necessary for operation of the computing device 900. The computing device 900 may also include a bus or other communication mechanism for communicating information among various components of the computing device 900.

Computing device 900 may have additional features/functionality. For example, computing device 900 may include additional storage such as removable storage 908 and non-removable storage 910 including, but not limited to, magnetic or optical disks or tapes. Computing device 900 may also contain network connection(s) 916 that allow the device to communicate with other devices. Computing device 900 may also have input device(s) 914 such as a keyboard, mouse, touch screen, etc. Output device(s) 912 such as a display, speakers, printer, etc. may also be included. The additional devices may be connected to the bus in order to facilitate communication of data among the components of the computing device 900. All these devices are well known in the art and need not be discussed at length here.

The processing unit 906 may be configured to execute program code encoded in tangible, computer-readable media. Tangible, computer-readable media refers to any media that is capable of providing data that causes the computing device 900 (i.e., a machine) to operate in a particular fashion. Various computer-readable media may be utilized to provide instructions to the processing unit 906 for execution. Example tangible, computer-readable media may include, but is not limited to, volatile media, non-volatile media, removable media and non-removable media implemented in any method or technology for storage of information such as computer readable instructions, data structures, program modules or other data. System memory 904, removable storage 908, and non-removable storage 910 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 906 may execute program code stored in the system memory 904. For example, the bus may carry data to the system memory 904, from which the processing unit 906 receives and executes instructions. The data received by the system memory 904 may optionally be stored on the removable storage 908 or the non-removable storage 910 before or after execution by the processing unit 906.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

This disclosure contemplates creating a physical eye model (e.g., a model that mimics the aphakic eye) including an ophthalmic lens. The physical eye model can be created based on the ophthalmic lens as evaluated according to any of the methods described herein. In some implementations, the ophthalmic lens is an IOL. This disclosure contemplates that the IOL can be any type of IOL. The physical eye model can further include a cornea, a pupil, a holder for the ophthalmic lens, a light source, and/or an electronic light sensor. An example physical eye model is described below with regard to FIG. 10. Characteristic(s) of the physical eye model can resemble optical characteristic(s) of the NSC ray-tracing model and/or the modelled light source described above with regard to FIGS. 2 and 3. Characteristics of the physical eye model can include, but are not limited to, cornea shape, ophthalmic lens dimensions, pupil and ophthalmic lens positioning, as well as characteristic(s) of the light source and/or light sensor. For example, characteristic(s) of the cornea, the pupil, and/or the ophthalmic lens can resemble optical characteristic(s) of the NSC ray-tracing model shown in FIG. 3, and characteristic(s) of the light source and/or the light sensor can resemble optical characteristic(s) of the modeled light source or modeled detector described above with regard to FIGS. 2 and 3.

This disclosure contemplates indirectly measuring edge frosting effect of an ophthalmic lens. For example, it is possible to obtain measurements using an off-axis modulation transfer function (MTF) bench, the physical eye model described herein, and an electronic light sensor. These measurements can be input into an NSC ray-tracing model (e.g., NSC ray-tracing model shown in FIG. 3). This method facilitates retro-fitting the edge frosting effect (e.g., the Lambertian scattering coefficient) through the NSC ray-tracing model.

Figure 10:
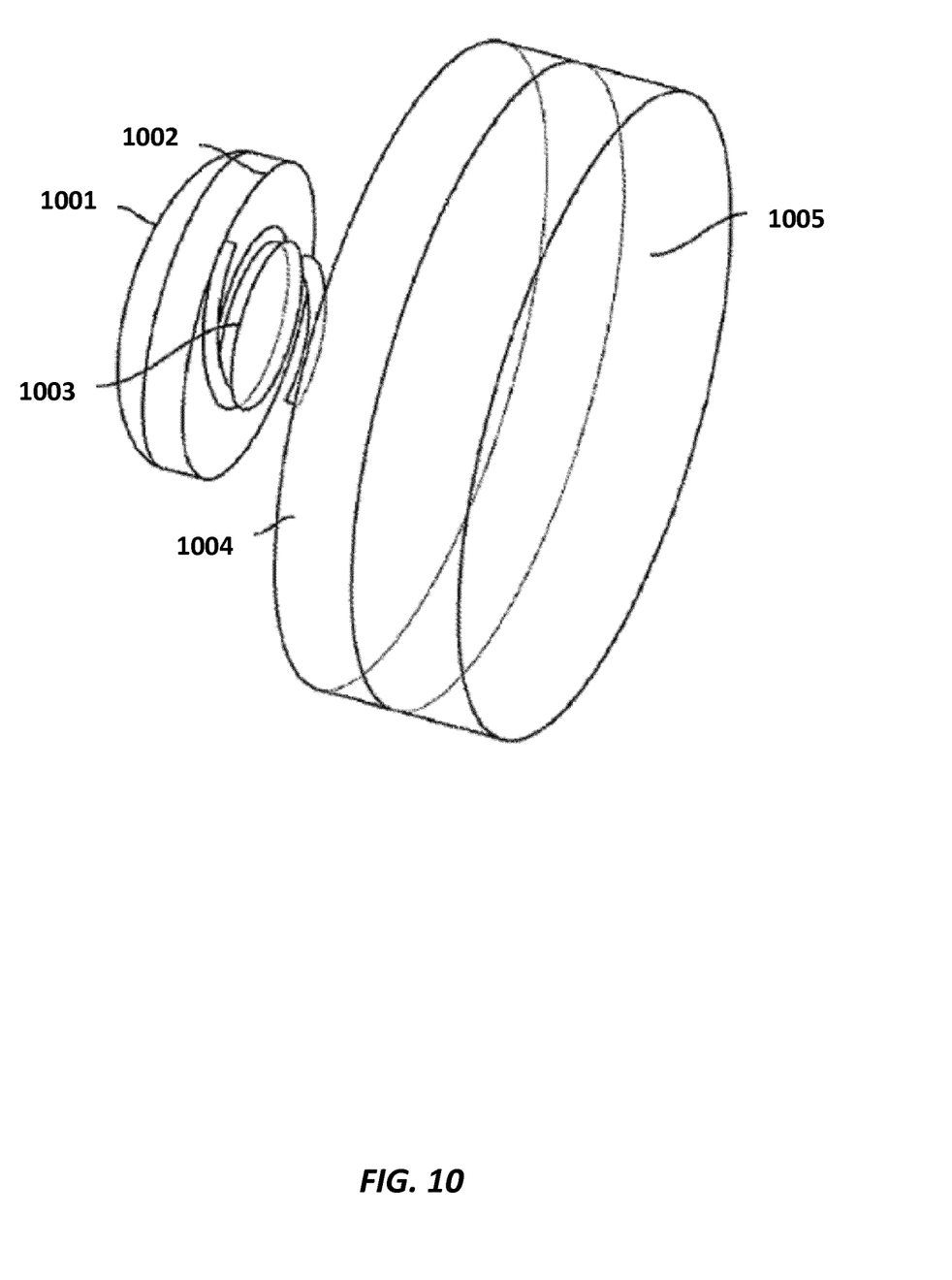
FIG. 10 is a diagram of a ray-tracing depiction of an example physical eye model according to an implementation described herein.

In some implementations, a set-up including a physical wide angle eye model can be constructed as depicted in FIG. 10. It includes a cornea 1001, a pupil 1002, an IOL holder with the IOL 1003, a back window 1004 and an electronic light sensor such as flat CCD camera 1005. The physical eye model is a ray-tracing based design to enable in-vitro visualization and quantification of various photic events (PD and ND). For a given object angle, pupil size and IOL design and position, the image heights associated with both main and spurious secondary images are theoretically calculated through non-sequential ray-tracing (e.g., the NSC ray-tracing model shown in FIG. 3). In order to realistically model the photic effects, a 3D CAD model of the IOL is used to account for its complete geometrical description. Defocusing wise, the native IOL field of curvature or a field of curvature giving an angular aberration profile identical to the one corresponding to the IOL placed in an individualized anatomical eye model with a unique or population averaged retinal shape (conicoid) could be used.

The electronic light sensors can comprise charged-coupled devices (CCD), including both imaging CCDs and intensity CCDs. In other embodiments complementary metal-oxide-semiconductor (CMOS) detectors can be used. In yet other embodiments a wavefront sensor such as a Shack-Hartmann wavefront sensor could be used. Finally, in some embodiments interferometers, photomultiplier tube (PMT) sensors, or small and large angle microscope sensors can be used. The light sensor can detect light emitted by a light source (not shown in FIG. 10).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A computer-implemented method, comprising:
constructing a non-sequential (NSC) ray-tracing model of an eye with an ophthalmic lens;
modelling a light source and a detector, wherein the detector is configured to mimic a retina of the eye and wherein the detector is a spherical or aspherical detector;
for each of a plurality of pupil sizes, computing irradiance data using the light source, the NSC ray-tracing model, and the detector; and
evaluating negative dysphotopsia (ND) by analyzing the respective irradiance data for each of the pupil sizes.

2. The computer-implemented method of claim 1, wherein analyzing the respective irradiance data for each of the pupil sizes comprises determining a retinal illumination gap between light refracted by the ophthalmic lens and light refracted only by a cornea of the eye.

3. The computer-implemented method of any one of claim 1 or 2, wherein the respective irradiance data in the temporal visual field is analyzed.

4. The computer-implemented method of any one of claims 1-3, wherein the irradiance data is at least one of an irradiance map or a cross-sectional irradiance profile.

5. The computer-implemented method of claim 4, wherein the irradiance data is a cross-sectional irradiance profile, the method further comprising deriving at least one of ND angular location, ND angular width, local contrast, or local area of reciprocal irradiance using the cross-sectional irradiance profile.

6. The computer-implemented method of any one of claims 1-5, further comprising constructing a sequential ray-tracing model of the eye using biometrical patient data.

7. The computer-implemented method of any one of claims 1-6, wherein the ophthalmic lens is modeled as a three-dimensional (3D) object.

8. The computer-implemented method of claim 7, further comprising generating a 3D model of the ophthalmic lens.

9. The computer-implemented method of any one of claim 7 or 8, further comprising adjusting the position or orientation of the 3D object within the eye.

10. The computer-implemented method of any one of claims 1-9, wherein the light source is a wide angle high divergence light source.

11. The computer-implemented method of claim 1, wherein the detector is defined by an aspheric equation.

12. The computer-implemented method of claim 1, wherein the detector is defined by a toric aspheric equation.

13. The computer-implemented method of any one of claims 1-10 and 11-12, further comprising:
constructing a respective NSC ray-tracing model of the eye with each of a plurality of ophthalmic lenses, wherein each of the ophthalmic lenses is configured for a different degree of edge scattering; and
for each of the pupil sizes, computing irradiance data using the light source, the respective NSC ray-tracing models, and the detector.

14. The computer-implemented method of claim 13, further comprising selecting an ophthalmic lens design that reduces ND from the plurality of ophthalmic lenses.

15. The computer-implemented method of any one of claims 1-10 and 11-14, further comprising:
constructing a respective NSC ray-tracing model of the eye with each of a plurality of ophthalmic lenses, wherein each of the ophthalmic lenses has a different edge thickness; and
for each of the pupil sizes, computing irradiance data using the light source, the respective NSC ray-tracing models, and the detector.

16. The computer-implemented method of claim 15, further comprising selecting an ophthalmic lens design that reduces ND from the plurality of ophthalmic lenses.

17. The computer-implemented method of any one of claims 1-10 and 11-16, wherein the ophthalmic lens is an intraocular lens (IOL).

18. A method for manufacturing an ophthalmic lens evaluated according to the method of any one of claims 1-10 and 11-17.

19. A method for creating a physical eye model including an ophthalmic lens evaluated according to the method of any one of claims 1-10 and 11-18.

20. The method of claim 19, wherein the physical eye model further includes at least one of a cornea, a pupil, a holder for the ophthalmic lens, a light source, or an electronic light sensor.

21. The method of claim 20, wherein a characteristic of at least one of the cornea, the pupil, or the ophthalmic lens resembles an optical characteristic of the NSC ray-tracing model.

22. The method of claim 20 or 21, wherein a characteristic of at least one of the light source or the electronic light sensor resembles an optical characteristic of the modeled light source or the modeled detector, respectively.

23. A method for indirectly quantifying edge frosting effect of an ophthalmic lens, comprising: obtaining measurements using an off-axis modulation transfer function (MTF) bench, the physical eye model according to any one of claims 19-22, and an electronic light sensor; and quantifying edge frosting effect of the ophthalmic lens by inputting the measurements into a non-sequential (NSC) ray-tracing model of an eye with an ophthalmic lens.

* * * * *